United States Patent [19]

Sterken et al.

[11] 4,431,840

[45] Feb. 14, 1984

[54] PROCESS FOR PREPARING 2-BENZOYLBENZOIC ACIDS

[75] Inventors: Gordon J. Sterken, Cincinnati, Ohio; Ramamurthi Kannan; James E. Kassner, both of Edgewood, Ky.

[73] Assignee: Sterling Drug Inc., New York, N.Y.

[21] Appl. No.: 436,003

[22] Filed: Oct. 22, 1982

[51] Int. Cl.$^3$ .......................................... C07C 101/78
[52] U.S. Cl. .................................................. 562/441
[58] Field of Search ................. 562/441; 549/308, 309

[56] References Cited

U.S. PATENT DOCUMENTS

| | | | |
|---|---|---|---|
| Re. 23,024 | 8/1948 | Adams ................................ | 562/458 |
| 3,491,112 | 1/1970 | Lin et al. ............................. | 562/441 |
| 3,577,439 | 5/1971 | McCormick et al. ............... | 562/441 |
| 3,658,964 | 4/1972 | Buzzolini et al. ................... | 424/317 |
| 4,045,458 | 8/1977 | Kondo et al. ....................... | 260/390 |
| 4,096,176 | 6/1978 | Crounse et al. ..................... | 562/441 |
| 4,168,378 | 9/1979 | Schmidt et al. ..................... | 549/303 |

FOREIGN PATENT DOCUMENTS 47-03468  1/1972  Japan .................................. 549/309

OTHER PUBLICATIONS

Doebner, Ann. 217, 257 (1883).
Wichelhaus, Chem. Ber. 19, 107–110 (1886).

*Primary Examiner*—Natalie Trousof
*Assistant Examiner*—Patricia M. Scott
*Attorney, Agent, or Firm*—Paul E. Dupont; B. Woodrow Wyatt

[57] ABSTRACT

Substituted 2-benzoylbenzoic acids, useful as intermediates for preparing valuable chromogenic phthalide compounds, are prepared by reacting certain substituted 3,3-diphenylphthalides with a lower alkanoic acid and water.

8 Claims, No Drawings

PROCESS FOR PREPARING 2-BENZOYLBENZOIC ACIDS

BACKGROUND OF THE INVENTION

1. Field of the Invention

The present invention pertains to a novel method of producing certain substituted 2-benzoylbenzoic acid derivatives which are useful as intermediates for preparing valuable chromogenic phthalide compounds.

2. Prior Art

Several structurally diverse types of organic compounds have been found useful as color formers for carbonless duplicating systems and thermal marking systems. Among the more important of these compounds are the phthalides, for example the 3,3-diarylphthalides disclosed in U.S. Pat. Nos. Re. 23,024 and 4,096,176, the 3-aryl-3-heteroarylphthalides disclosed in U.S. Pat. Nos. 3,491,112 and 4,045,458, and the 3-aryl-3-(diarylamino)phthalides disclosed in U.S. Pat. No. 4,168,378. Of the several methods disclosed for preparing these compounds, the most versatile appears to be the reaction of a 2-benzoylbenzoic acid with an aniline derivative, an aromatic heterocyclic nitrogen compound or a diarylamine derivative to produce respectively a 3,3-diarylphthalide, a 3-aryl-3-heteroarylphthalide or a 3-aryl-3-(diarylamino)phthalide. Thus this method permits the preparation of a wide variety of phthalide color formers from a single intermediate in a one step reaction. Unfortunately however, when applied to the preparation of phthalides containing substituents in the phthalide ring, the apparent advantages of this process are significantly diminished because the requisite substituted 2-benzoylbenzoic acid intermediates, which are ordinarily obtained by reacting an appropriate substituted phthalic anhydride with an aniline derivative, are not readily accessible. The synthesis of substituted phthalic anhydrides is complex and unsuited to industrial production, and moreover, as would be expected, the reaction of a substituted phthalic anhydride with an aniline derivative produces a mixture of isomeric substituted 2-benzoylbenzoic acids. Thus there is need for a simple and economical method of producing pure substituted 2-benzoylbenzoic acids in high yield.

The following references appear to constitute the most pertinent prior art relative to the instant invention.

Doebner, Ann. 217, 257 (1883), discloses the reaction of malachite green with sulfuric acid to give 4-(dimethylamino)-benzophenone.

Wichelhaus, Chem. Ber. 19, 107–110 (1886), discloses the acid hydrolysis of crystal violet to give 4-4'-bis(dimethylamino)benzophenone (Michler's ketone).

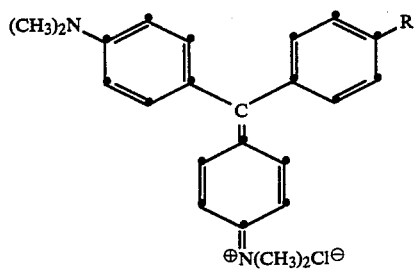

malachite green: R = H

Crystal violet: R = N(CH$_3$)$_2$

SUMMARY OF THE INVENTION

It is an object of the present invention to overcome the above-mentioned problems in the prior art by providing a novel method of producing 5-R$_1$R$_2$N-2-[4-(R$_3$R$_4$N)benzoyl]benzoic acids which comprises reacting a 3-[4-(R$_3$R$_4$N)phenyl]-3-(2-Y-4-Z-phenyl)-6-R$_1$R$_2$N-phthalide with a lower alkanoic acid and water.

DETAILED DESCRIPTION INCLUSIVE OF THE PREFERRED EMBODIMENTS

More particularly the invention sought to be patented resides in a process for preparing a 2-benzoylbenzoic acid derivative having formula I:

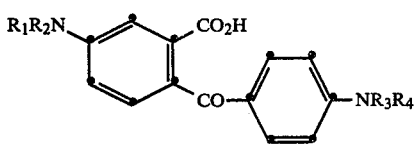

which comprises reacting a phthalide derivative having formula II:

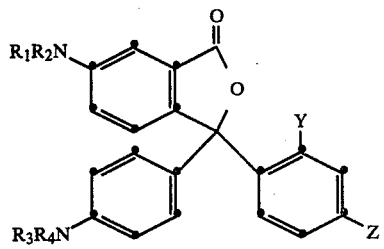

with a lower alkanoic acid and water, where in the above formulas:

R$_1$, R$_2$, R$_3$ and R$_4$ are the same or different non-tertiary lower alkyl;

Y is hydrogen and Z is NR$_3$R$_4$, or

Y is non-tertiary lower alkyl, non-tertiary lower alkoxy or di-lower-alkylamino and Z is di-lower-alkylamino.

The compounds of formula I are intermediates for preparing various phthalide derivatives which are useful as color formers in pressure-sensitive carbonless duplicating systems and thermal marking systems.

As used herein the term "non-tertiary lower alkyl" denotes saturated, monovalent, straight or branched aliphatic hydrocarbon radicals including methyl, ethyl, propyl, isopropyl, butyl, sec-butyl, and isobutyl.

Similarly the term "non-tertiary lower alkoxy" includes saturated acyclic straight or branched-chain groups such as methoxy, ethoxy, propoxy, isopropoxy, butoxy, sec-butoxy, and isobutoxy.

The term "di-lower-alkylamino" denotes a nitrogen atom substituted by two saturated acyclic groups having from 1 to 4 carbon atoms which may be straight or branched and is exemplified by dimethylamino, diethylamino, ethylmethylamino, dipropylamino, dibutylamino, isobutylmethylamino and the like.

As used herein the term "lower alkanoic acid" denotes an aliphatic carboxylic acid containing from 1 to 4 carbon atoms which may be straight or branched as exemplified by formic, acetic, propionic, butyric, and isobutyric acid. Acetic acid is preferred because of its relatively low cost and ready availability.

In accordance with the present invention a mixture containing a phthalide of formula II, a lower alkanoic acid and water is heated at about 90°–150° C. for approximately 1 to 72 hrs. Ordinarily the reaction is carried out by heating the phthalide in 75–95% aqueous alkanoic acid, preferably aqueous acetic acid, under reflux. Although water is necessary for the reaction to take place, diluting the acid below about 75% significantly reduces the rate of reaction. Hence it is preferred to carry out the reaction in about 85% aqueous acetic acid. Similarly the reaction takes place rather sluggishly below about 90° C. and it is therefore preferred to carry out the reaction at the reflux temperature of the reaction medium, i.e. at about 100°–115° C. Although the amount of aqueous acid can vary rather widely from about 2 to about 5 parts by weight relative to the phthalide, it is usually advantageous to use the minimum amount in order to facilitate isolation of the 2-benzoylbenzoic acid by precipitation from the cooled reaction mixture. Accordingly the reaction is preferably carried out using about 2 parts by weight of aqueous acetic acid. Progress of the reaction can be monitored by thin layer chromatography, and when complete the 2-benzoylbenzoic acid can be isolated in conventional fashion. Ordinarily the product precipitates on cooling the reaction mixture and is collected by filtration. The 2-benzoylbenzoic acid thus obtained can be used directly as a starting material in the preparation of phthalide color formers or if desired it can be further purified by recrystallization.

The starting materials for the present process, i.e. the phthalides of formula II are known compounds which can be prepared by known methods, for example, as taught by U.S. Pat. No. 4,045,458. A preferred starting material is 3,3-bis-[4-(dimethylamino)phenyl]-6-(dimethylamino)phthalide also known as crystal violet lactone or CVL. This material is commercially available and is relatively inexpensive. It is readily prepared from m-(dimethylamino)benzoic acid and 4,4'-bis-(dimethylamino)benzhydrol (Michler's hydrol) as described in U.S. Pat. No. Re. 23,024. Thus in a preferred embodiment of the present invention, crystal violet lactone is reacted with approximately 2 parts by weight of 85% aqueous acetic acid under reflux to give 5-(dimethylamino)-2-[4-(dimethylamino)-benzoyl]benzoic acid, the compound of formula I wherein $R_1$, $R_2$, $R_3$ and $R_4$ are each methyl.

The substituted 2-benzoylbenzoic acids afforded by the process of this invention can be reacted with various aniline derivatives, with aromatic heterocyclic nitrogen compounds such as indoles, pyrroles and carbazoles or with various diphenylamine derivatives to produce valuable phthalide color formers as described in U.S. Pat. Nos. 4,096,176, 3,491,112, and 4,168,378.

The identities of the 2-benzoylbenzoic acids of formula I were confirmed by comparison with authentic samples prepared by published procedures.

The following examples will further illustrate the invention without however limiting it thereto.

EXAMPLE 1

A. A mixture containing 1200.0 g. of 6-(dimethylamino)-3,3-bis[4-(dimethylamino)phenyl]phthalide (commonly known as crystal violet lactone or CVL) 1945 ml. of glacial acetic acid and 360 ml. of water was heated under reflux for 68 hrs. The reaction mixture was cooled to 0° C. and stirred 1 hr. at 0°–5° C. The resulting solid product was collected by filtration, washed thoroughly with isopropyl alcohol and dried under vacuum at 70°–80° C. to afford 671.8 g. of 5-(dimethylamino)-2-[4-(dimethylamino)benzoyl]benzoic acid, m.p. 274°–277° C.

B. A mixture containing 320 g. of crystal violet lactone, 815.2 g. of glacial acetic acid and 143.9 g. of water was heated under reflux for 48 hrs. The reaction mixture was cooled to room temperature and the resulting solid was collected by filtration, washed thoroughly with methanol and dried under vacuum at 70°–80° C. to give 167.6 g. of 5-(dimethylamino)-2-[4-(dimethylamino)benzoyl]benzoic acid.

C. Following a procedure similar to that described in Part B above but employing 320.0 g. of crystal violet lactone, 544.0 g. of glacial acetic acid and 96 ml. of water, there was obtained 172 g. of 5-(dimethylamino)-2-[4-(dimethylamino)benzoyl]benzoic acid. A second crop of 56.3 g. was obtained by further refluxing the mother liquors overnight, cooling the reaction mixture and diluting with water to precipitate the product.

EXAMPLE 2

A mixture containing 40 g. of crystal violet lactone, 153 g. of formic acid and 27 g. of water was heated under reflux for 18 hrs. The reaction mixture was cooled to 40° C. and the resulting solid was collected by filtration, washed with methanol and dried to give 4.1 g. of 5-(dimethylamino)-2-[4-(dimethylamino)benzoyl]-benzoic acid.

EXAMPLE 3

A mixture containing 80 g. of 6-(dimethylamino)-3-[4-(dimethylamino)phenyl]-3-[2,4-bis(dimethylamino)-phenyl]phthalide and 360 g. of 85% by weight aqueous acetic acid was heated under reflux over the weekend. The reaction mixture was cooled to room temperature and the resulting solid was collected by filtration, washed thoroughly with isopropyl alcohol and dried under vacuum at 70°–80° C. to yield 15.8 g. of 5-(dimethylamino)-2-[4-(dimethylamino)benzoyl]benzoic acid, m.p. 271°–273° C., mixed m.p. with the product of Example 1A 273°–274° C.

EXAMPLE 5

A mixture containing 20 g. of 6-(dimethylamino)-3-[4-(dimethylamino)phenyl]-3-[2-ethoxy-4-(dimethylamino)phenyl]phthalide, 73 ml. of glacial acetic acid and 13.5 ml. of water was heated under reflux for approximately 1 hr. The reaction mixture was cooled to 27° C. and the resulting solid was collected by filtration, washed with isopropyl alcohol and dried under vacuum at 80° C. to give 11.84 g. of 5-(dimethylamino)-2-[4-(dimethylamino)benzoyl]benzoic acid.

We claim:

1. A process for preparing a 2-benzoylbenzoic acid derivative having the formula

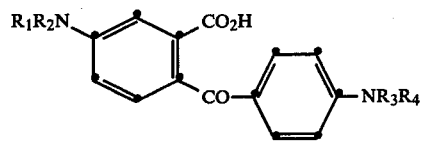

which comprises reacting a phthalide derivative having the formula

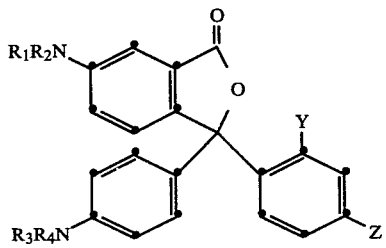

with a lower-alkanoic acid and water where in the above formulas:

$R_1$, $R_2$, $R_3$ and $R_4$ are the same or different non-tertiary lower alkyl, Y is hydrogen and Z is $NR_3R_4$, or Y is non-tertiary lower alkyl, non-tertiary lower alkoxy or di-lower-alkylamino and Z is di-lower-alkylamino.

2. A process according to claim 1 wherein said phthalide derivative is reacted with 75–95% aqueous acetic acid at about 100°–150° C.

3. A process according to claim 2 wherein said phthalide derivative is reacted with 85% aqueous acetic acid under reflux.

4. A process according to claim 1 wherein $R_1$, $R_2$, $R_3$ and $R_4$ are each methyl.

5. A process according to claim 4 wherein Y is methyl, ethoxy or dimethylamino and Z is dimethylamino or diethylamino.

6. A process according to claim 4 wherein Y is hydrogen and Z is dimethylamino.

7. A process according to claim 6 wherein said phthalide derivative is reacted with 75–95% aqueous acetic acid at about 100°–150° C.

8. A process according to claim 7 wherein said phthalide derivative is reacted with 85% aqueous acetic acid under reflux.

* * * * *